United States Patent [19]

Abernathy

[11] Patent Number: 4,945,918

[45] Date of Patent: Aug. 7, 1990

[54] METHOD AND APPARATUS FOR MONITORING A PATIENT'S CIRCULATORY STATUS

[76] Inventor: Charles M. Abernathy, 2420 E. Miami Rd., Montrose, Colo. 81401

[21] Appl. No.: 189,977

[22] Filed: May 4, 1988

[51] Int. Cl.[5] ............................................... A61B 5/08
[52] U.S. Cl. ............................... 128/719; 128/202.13;
128/202.22; 128/205.23; 128/671
[58] Field of Search ............... 128/236, 716, 719, 725,
128/727, 202.22, 205.23, 202.13, 671; 116/200,
201, 206, 209; 922/3-5, 84-89, 103, 104;
436/133

[56] References Cited

U.S. PATENT DOCUMENTS

| | | | |
|---|---|---|---|
| 3,659,586 | 5/1972 | Johns et al. | 128/716 |
| 4,346,584 | 8/1982 | Boehringer | 73/23 |
| 4,366,821 | 1/1983 | Wittmaier et al. | 128/719 |
| 4,619,269 | 10/1986 | Cutler et al. | 128/719 |
| 4,691,701 | 9/1987 | Williams | 128/207.14 |
| 4,728,499 | 3/1988 | Fehder | 422/56 |
| 4,790,327 | 12/1988 | Despotis | 128/719 |

OTHER PUBLICATIONS

MSA Company Brochure: "Vaporgard", Pittsburgh, Pa.

M. G. Lepilin, M.D. et al.; "End-Tidal Carbon Dioxide as a Noninvasive Monitor of Circulatory Status During Cardiopulmonary Resuscitation; A Preliminary Clinical Study", vol. 15, No. 10, 1987.

S. Dohi, M.D. et al.: "Carbon Dioxide Elimination During Circulatory Arrest".

A. R. Garnett, M.D. et al.: "End-Tidal Dioxide Monitoring During Cardiopulmonary Resuscitation", vol. 257, No. 4, Jan. 23/30, 1987.

Primary Examiner—Randall L. Green
Assistant Examiner—K. M. Reichle
Attorney, Agent, or Firm—Brian D. Smith

[57] ABSTRACT

A method and apparatus for monitoring a patient's circulatory status during cardiopulmonary resuscitation is disclosed. The apparatus includes a housing defining a passageway through which the patient's breath passes. The device also includes a carbon dioxide indicator in communication with said passageway for indicating the presence of carbon dioxide in the patient's breath over a temporary period of time wherein the length of the temporary period is a known function of the level of carbon dioxide in the patient's breath. Accordingly, the level or concentration of carbon dioxide in the patient's breath is easily determined by simply measuring the length of the temporary period. The preferred carbon dioxide indicator utilizes a chemical substance that changes color when exposed to carbon dioxide. The chemical substance is preferably disposed in an internal chamber which is in communication with the housing's passageway. The internal chamber is preferably sized and configured to contain a predetermined amount of the chemical substance so that all of the substance changes color over a period of about four minutes when exposed to the breath of a patient containing about 1% carbon dioxide.

18 Claims, 2 Drawing Sheets

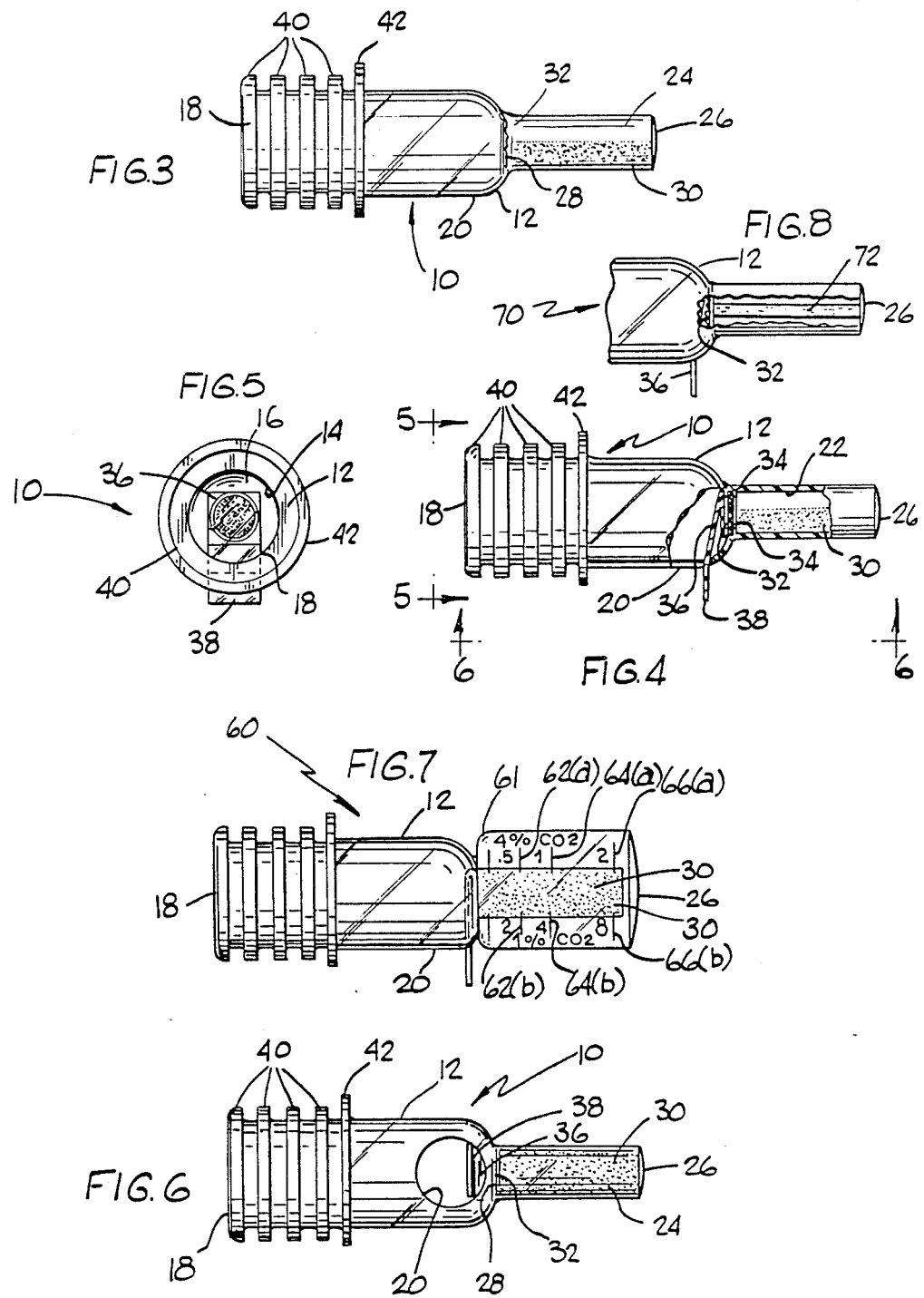

METHOD AND APPARATUS FOR MONITORING A PATIENT'S CIRCULATORY STATUS

Field of the Invention

The invention relates in general to method and apparatus for detecting the presence of carbon dioxide and, more particularly, to method and apparatus for monitoring a patient's circulatory status during cardiopulmonary resuscitation by measuring the level of carbon dioxide in the patient's breath.

BACKGROUND OF THE INVENTION

The relationship between the level of carbon dioxide in the expired air or breath of a patient being resuscitated and the patient's circulatory status was the subject of experimental studies recently conducted and reported by Drs. Lepilian, Vasilyev, Bildinov and Rostovtseva, in a report entitled "End-Tidal Carbon Dioxide as a Noninvasive Monitor of Circulatory Status During Cardiopulmonary Resuscitation: A Preliminary Clinical Study" which was published in Critical Care Medicine Volume 15, No. 10, (1987). The studies were conducted on four patients during controlled ventilation, six to eight hours after aortocoronary bypass surgery. Each patient was mechanically ventilated with an oxygen-air mixture at an inspired oxygen fraction of 0.4. Expiratory carbon dioxide was monitored continuously with an infrared carbon dioxide analyzer. The report concluded that end tidal carbon dioxide concentration measurements taken during controlled ventilation of a patient experiencing acute circulatory failure can be used as an indirect noninvasive monitoring tool to assess the patient's circulatory status during cardiopulmonary resuscitation (CPR).

In view of this relationship between circulatory status and the level of carbon dioxide present in a patient's breath, it would be desirable if a device were available that is readily attachable to existing CPR equipment used by paramedics in the field. Such a device would preferably enable paramedics administering CPR to readily determine the level of carbon dioxide in a patient's breath. If the level of $CO_2$ in the patient's breath were to drop below 1% "a level determined to be critical for adequate resuscitation" such a device would preferably promptly alert the paramedic to such, thereby providing the paramedics with more time (i.e., much needed time) to take whatever steps are necessary to save the patient's life.

U.S. Pat. No. 4,691,701 to Williams discloses a device which enables a paramedic to determine whether a patient's trachea has been properly intubated with an endotracheal tube (i.e., has the endotracheal tube been properly inserted into the trachea and not the esophagus). The device utilizes a chemical indicator which changes color when exposed to carbon dioxide. The device is added to an anaesthetic circuit and one expiration by the patient will instantly change the color of the indicator, thereby indicating that the trachea has been properly intubated, especially in conjunction with other signs.

Mine Safety Appliances brochure number 470243 discloses a device referred to as a dosimeter tube for detecting the presence of carbon dioxide in a mine. The dosimeter tube contains an acid base indicator which slowly changes color along the length of a tube when the end of the tube is broken, thereby exposing the indicator to carbon dioxide in the mine. The speed at which the indicator changes colors is proportional to the level of carbon dioxide in the mine. Accordingly, a high level of carbon dioxide in the mine will cause the indicator to change color along the length of the tube more quickly than a low level will. In determining such level, the miner measures the length of the indicator stain which has changed color and the period of time that has passed since the tube was broken. The miner then resorts to a precalibrated graph wherein the precise level is indicated as a function of stain length and time.

Other devices for carbon dioxide detection are disclosed in U.S. Pat. Nos. 4,619,269, 4,346,584 and 4,366,821.

While the aforementioned devices undoubtedly work as intended, there remains a need for a device that will enable paramedics to monitor the circulatory status of a patient being resuscitated in the field. Such a device would preferably be portable and readily attachable to existing equipment used by paramedics in the field.

SUMMARY OF THE INVENTION

The present invention addresses the aforementioned concerns by providing a portable device for monitoring a patient's circulatory status during cardiopulmonary resuscitation. The device includes a housing defining a passageway through which the patient's breath passes. As used herein, breath means expired or exhaled air from a patient being resuscitated. Also included is means in communication with said passageway for indicating the presence of carbon dioxide (i.e., $CO_2$) in the patient's breath over a temporary period wherein the length of the temporary period is a known function of the level of carbon dioxide in the patient's breath. Accordingly, the level or concentration of $CO_2$ in the patient's breath is easily determined by simply measuring the length of the temporary period. If the level of $CO_2$ in the patient's breath is below about 1%, other steps to resuscitate the patient must be taken inasmuch as $CO_2$ levels below 1% indicate that the resuscitation effort is inadequate.

In a preferred embodiment of the present invention, the means for indicating the presence of carbon dioxide includes a chemical substance that changes color when exposed to carbon dioxide. The preferred embodiment also includes an internal chamber in communication with the housing's passageway. The internal chamber is preferably sized and configured to contain a predetermined amount of the aforementioned chemical substance so that all of the substance will change color over a period of about four minutes when exposed to a patient's breath containing about 1% carbon dioxide.

In another embodiment of the present invention, the aforementioned internal chamber is completely filled with a chemical substance to provide a column of chemical substance that changes color along the column when it is exposed to carbon dioxide. This embodiment also includes a scale attached to that part of the housing defining the internal chamber which enables medical personnel to readily determine the level of carbon dioxide in the patient's breath by simply measuring the period of time that has passed after putting the device into use.

Yet another embodiment of the present invention includes chemical means, preferably pH dependent chemical means, in communication with the aforementioned passageway of the device for separately analyzing each breath of the patient to determine whether each breath contains a predetermined minimum level of carbon dioxide.

The present invention also provides a method for monitoring the patient's circulatory status during cardiopulmonary resuscitation. The method includes providing a housing defining a passageway through which the patient's breath passes and providing means in communication with the passageway for indicating the presence of carbon dioxide in the patient's breath over a temporary period of time wherein the length of the temporary period is a known function of the level of carbon dioxide in the patient's breath. The method further includes measuring the length of the temporary period to determine the level of carbon dioxide in the patient's breath, the level of carbon dioxide thereby providing an indication of the patient's circulatory status.

BRIEF DESCRIPTION OF THE DRAWINGS

Other features of this invention will appear in the following description and appended claims, reference being made to the accompanying drawings forming a part of the specification where like referenced characters designate corresponding parts in the views.

FIG. 3 is a side elevational view of the device illustrated in FIG. 2.

FIG. 4 is a side elevational view of the device of FIG. 2 showing a portion of the device broken away to illustrate the sealing pull-tab feature of the device.

FIG. 5 is an end view of the device taken along lines 5—5 of FIG. 4.

FIG. 6 is a bottom plan view of the device taken along lines 6—6 of FIG. 4.

FIG. 7 is side elevational view of an alternative embodiment of the present invention which is provided with a scale from which the level of $CO_2$ in the patient's expired air can be readily determined.

FIG. 8 is a side elevational view of an another embodiment of the present invention showing a portion of the device broken away to illustrate a chemical strip that separately analyzes each breath of a patient being resuscitated.

DETAILED DESCRIPTION OF THE DRAWINGS

Figure 1:
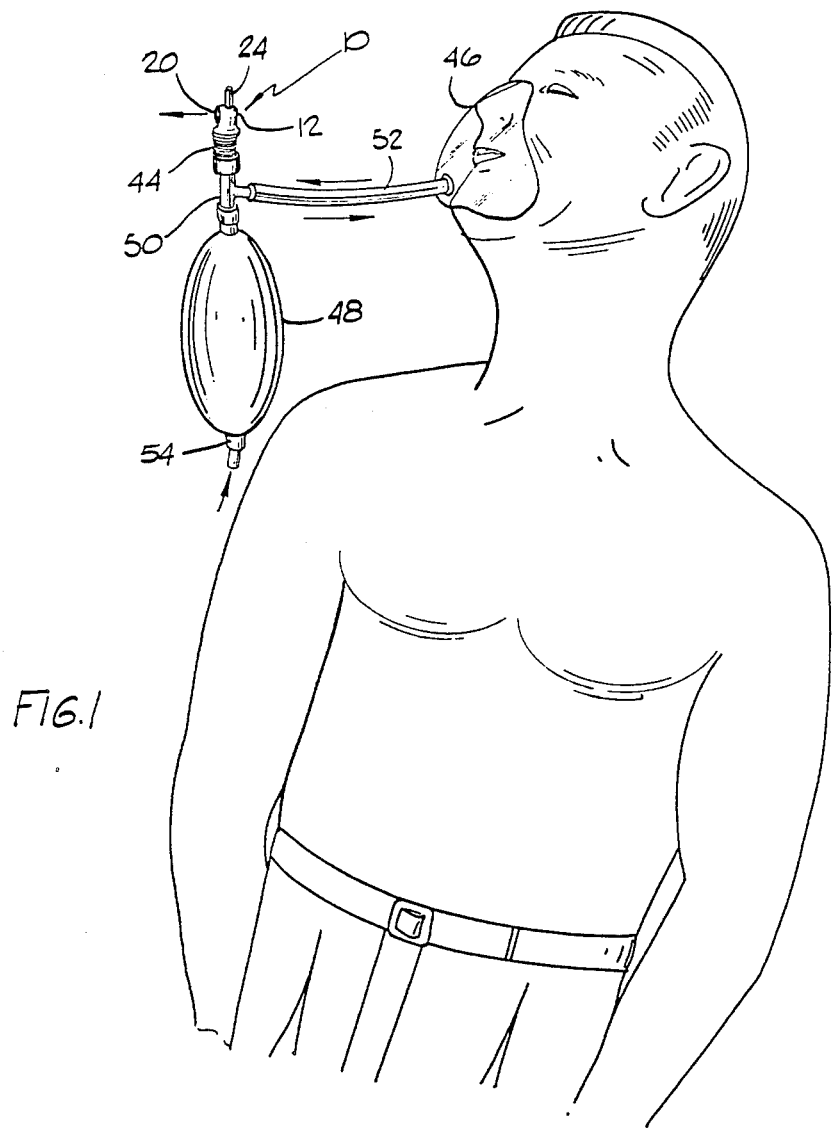
FIG. 1 is a perspective view of a device of the present invention attached to the expired air side of a conventional ambulatory bag and mask system which is being used to resuscitate a patient experiencing cardiac arrest.
Figure 2:
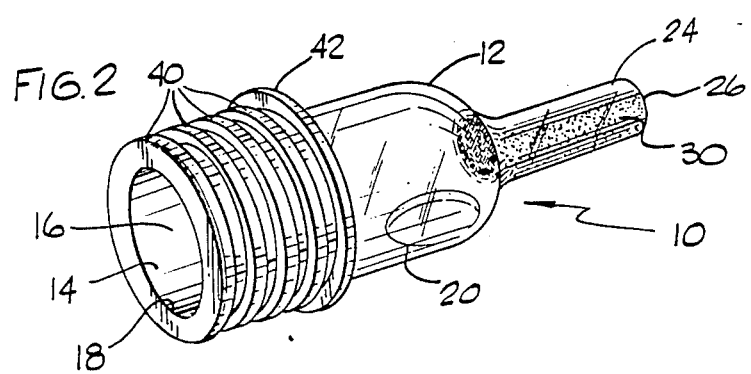
FIG. 2 is a perspective view illustrating the device of FIG. 1 in isolation.

FIGS. 1 through 6 illustrate a portable resuscitation monitor or device 10 of the present invention. Device 10 includes a housing 12 which is preferably made from a moldable transparent plastic such as an acrylic. Housing 12, as illustrated, has a generally cylindrically shaped inner surface 14 which defines a hollow internal passageway 16. Passageway 16 has an inlet 18 (also defined by surface 14) for receiving a patient's breath and an outlet 20 (also defined by surface 14) for discharging the patient's breath.

Housing 12 also has another inner surface 22 defining a generally cylindrically shaped internal chamber 24. Internal chamber 24 has a closed end 26 and a sealable end 28 which when not sealed (as will be explained in more detail below) puts internal chamber 24 in communication with passageway 16.

Internal chamber 24 is also preferably sized and configured to contain a predetermined amount of chemical substance 30 that completely changes color over about a four minute period when exposed to expired air or breath of the patient containing about 1% carbon dioxide. Substance 30 also preferably changes color at a rate which is proportional to the level of carbon dioxide in the patient's breath. Accordingly, if all of substance 30 changes color in less than four minutes, the patient's breath must contain more than 1% $CO_2$. This is a positive sign indicating that the patient is being adequately resuscitated. If it takes all of substance 30 more than four minutes to change color, the patient's breath must contain less than 1% carbon dioxide. This indicates that the resuscitation effort is not proceeding adequately and that other steps should be taken to save the patient's life if, of course, the patient is still alive. The four minute period for indicating the presence of 1% carbon dioxide is preferred because it is long enough to enable one to obtain a relatively accurate assessment of the patient's circulatory status. Measurements taken over a shorter period such as thirty seconds, while informative, would not generally be as accurate and a longer period would rob the paramedic of precious time in which to save the patient's life if the patient is not being adequately resuscitated.

FIG. 4 illustrates that chemical substance 30 is retained in internal chamber 24 by a screen 32 which is mounted across sealable end 28. Screen 32 is preferably provided with mesh of a size that permits the unobstructed flow of the patient's breath into the internal chamber but substantially prevents substance 30 from entering passageway 16.

Screen 32 is mounted across sealable end 28 by snapping it into a groove 34 which extends circumferentially around open end 28. While not shown, screen 32 could also be mounted across end 28 by mounting it in a plastic frame which is then glued to end 28.

FIG. 4 also illustrates a sealing pull-tab 36 which is sized and configured and provided with a suitable adhesive on one side thereof to sealingly cover end 28 of internal chamber 24. Sealing tab 36 is also provided with an end 38 which extends out through outlet 20 when the tab is sealably affixed to open end 28 and folded back over end 28 as illustrated. By extending out through outlet 20, end 38 is easily grasped when it is desired to use the device as will be explained below.

Housing 12 further defines a series of four ribs 40 and a stop 42 which extend circumferentially about the housing's outer surface (not numbered) adjacent inlet 18. Ribs 40 and stop 42 provide a means for attaching inlet 18 of the device to a flexible hose member such as a hose coupling or connector 44 of the conventional ambulatory bag-mask system illustrated in FIG. 1. Such attachment is provided by simply inserting the end of housing 12 defining ribs 40 into the open end of the connector until the end of the connector rests up against stop 42. Ribs 40 provide an air tight seal between the connector and device 10 since they are sized to sealingly engage with the inside wall of the connector.

In using device 10 of the present invention after attaching it to the ambulatory bag mask system illustrated in FIG. 1, an individual such as a paramedic first removes sealing pull-tab 36 from open end 28 of the device to expose chemical substance 30 disposed in internal chamber 24. Mask 46 of the ambulatory bag-mask system should then be placed immediately over the nose and mouth of the patient as illustrated in FIG. 1. The paramedic should also begin clocking or measuring time which passes from this point. The patient should then be ventilated by squeezing or pressing bag 48 of the system which hopefully forces air contained in bag 48 into the lungs of the patient via a conventional non-rebreathing valve 50, tube 52 and mask 48 of the ambu bag-mask system. The bag is then released whereupon it elastically returns to its nonpressed or squeezed state, the return of which also draws outside air into the bag via one way valve 54. As the bag is refilling, the patient is hopefully expiring or exhaling air from his or her lungs. The patient's expired air or breath passes through mask 46, tube 52 and valve 50 into passageway 16 of the device via inlet 18. The patient's breath then passes through passageway 16 and is discharged from passageway 16 via outlet 20.

Some of the patient's breath passing through passageway 16 will pass into internal chamber 24 containing substance 30 since pull-tab 36 has been removed. Accordingly, chemical substance 30 will begin changing color immediately if the patient's breath contains any appreciable amount of carbon dioxide. If all of chemical substance 30 changes color in about four minutes after beginning the aforesaid time measurement, the patient's breath contains about 1% $CO_2$, thereby indicating, as previously mentioned, that the resuscitation process is proceeding adequately. If it takes the chemical substance more than four minutes to completely change color, the patient's breath contains less than 1% carbon dioxide, thereby indicating that the resuscitation process is not proceeding adequately. Accordingly, the paramedic should at this point take other steps to resuscitate the patient such as intubating the patient's trachea with an endotracheal tube and/or possibly opening the patient to internally massage the patient.

The device of the present invention can also be used with an endotracheal tube ventilating system. Accordingly, if it is decided that the patient should be ventilated with an endotracheal tube, a new unused device 10 should be attached to the expired air side of the endotracheal tube system to monitor this resuscitation effort.

A chemical substance that has been found to change color as desired in about four minutes when exposed to a patient's breath containing 1% carbon dioxide and disposed in internal chamber 24 so that it fills the chamber about half way as illustrated in FIGS. 1 through 6 is 0.03 grams of a 1:10 mixture of thymol blue and ethanol amine.

A screen 32 which has been found to permit adequate air flow therethrough and yet retain the aforementioned mixture of thymol blue and ethanol amine in internal chamber 24 is a copper screen having mesh of a size ranging between #40 and #80, preferably about #60 mesh.

FIG. 7 illustrates another embodiment 60 of the present invention which is identical to that illustrated in FIGS. 1 through 6 except in two respects. The first difference is that internal chamber 24 of this embodiment is completely filled with a chemical substance 30 to provide a column of chemical substance that will change color along the column from left to right as illustrated in FIG. 7 when exposed to $CO_2$. The second difference is that this embodiment additionally includes a scale 61 which enables the paramedic or other medical personnel to readily determine the level of $CO_2$ in the patient's breath by simply measuring or clocking the period of time that has passed after putting the device into use (i.e., after attaching the device to the expired air side of a suitable ventilating means and removing sealing pull-tab 36).

Scale 61 is calibrated with three parallel sets of time indicating marks 62 (a) and (b), 64 (a) and (b) and 66 (a) and (b) Marks 62(a), 64(a) and 66(a) located on the top portion of the scale are labelled with time periods for indicating whether the patient's breath contains 4% $CO_2$. Marks 62(b), 64(b) and 66(b) located on the bottom portion of the scale are labelled with time periods for indicating whether the patient's breath contains 1% $CO_2$. 1% $CO_2$ as previously mentioned, is the minimum level of $CO_2$ necessary for adequate resuscitation. A reading of 4% $CO_2$ indicates that the patient is breathing normally and has been completely resuscitated.

To read scale 61, one simply records the time it takes that portion of the column indicated (or set off) by any of the marks 62, 64 and 66 to change color (i.e., reach the marks). Accordingly, if the portion of the column indicated by marks 62 changes color (i.e., reaches marks 62) in thirty seconds, i.e., .5 minutes, the patient's breath contains 4% carbon dioxide. If it takes two minutes to reach marks 62, the patient's breath contains only 1% carbon dioxide. If it takes some time between thirty seconds and two minutes to reach marks 62 then the paramedic will know that the level of $CO_2$ in the patient's breath is somewhere between 1 and 4% and that the resuscitate effort is proceeding adequately. On the other hand, if it takes the column of color changing substance longer than two minutes to reach the marks 62, the patient's breath contains less than 1% $CO_2$. This, as previously mentioned, means that the patient is not being adequately resuscitated and that other steps to resuscitate the patent should be taken.

The second and third parallel sets of marks (i.e., marks 64 (a) and (b) and 66 (a) and (b)) on the scale also provide for continued monitoring of the patient's circulatory status and can be used to determine whether the patient's circulatory status is improving. For example, if it takes the color changing column two minutes to reach first marks 62 and yet only one minute to reach second marks 64, this indicates that the resuscitation process is adequate and that the patient's circulatory status is actually improving. On the other hand, if it takes more time for the column to reach second marks 64 than first marks 62, this might indicate that the resuscitation process is not proceeding adequately and that the patient's circulatory status is deteriorating. Accordingly, the paramedics at this point would be well advised to take other steps to resuscitate the patient.

FIG. 8 illustrates another embodiment 70 of the present invention wherein a chemical means or chemical strip 72 is disposed in internal chamber 24 instead of chemical substance 30. Chemical means 72 separately analyzes each breath of the patient to determine whether each breath contains a predetermined minimum level of carbon dioxide such as, for example, 1% carbon dioxide. Chemical means 72 is also preferably pH dependent and preferably analyzes each breath by changing back and forth between two colors with each breath if the breath contains the minimum level of carbon dioxide, i.e., 1% carbon dioxide. For example, if chemical means 72 is blue in normal ambient air, it will remain blue if the patient's breath does not contain 1% carbon dioxide. If the patient's breath contains 1% carbon dioxide, chemical means 72 will change color, for example, from blue to white. Chemical means 72 is also sensitive enough to change back to blue between breaths when ambient or normal air again covers or surrounds it. Accordingly, chemical means 70 has the ability to prepare itself for the patient's next breath. This embodiment of the present invention is advantageous since it enables paramedics to take extremely quick action, if, for example, ten or fifteen breaths of the patient pass in a row without changing the color of the chemical means.

This invention has been described in detail with reference to particular embodiments thereof, but it will be understood that various other modifications can be effected within the spirit and scope of this invention.

What is claimed is:

1. An apparatus for monitoring a patient's circulatory status during cardiopulmonary resuscitation comprising:

a housing defining carbon dioxide indicating passageway means for passing the patient's breath and means in communication with said passageway means for indicating the presence of carbon dioxide in the patient's breath over a temporary period wherein the length of the temporary period of indicating is a known function of the level of carbon dioxide in the patient's breath so that the carbon dioxide level is determinable by measuring the length of the temporary period, the level of carbon dioxide thereby providing an indication of the patient's circulatory status.

2. An apparatus as claimed in claim 1 wherein said housing defines an internal chamber in communication with said passageway, means said means for indicating the presence of carbon dioxide being disposed within said internal chamber.

3. An apparatus as claimed in claim 2 wherein said chamber is cylindrically shaped with the portion of said housing defining said internal chamber being transparent.

4. An apparatus as claimed in claim 1 wherein said carbon dioxide indicating means further includes:

scale means for indicating whether the patient's breath contains a specific percentage of carbon dioxide.

5. An apparatus as claimed in claim 1 wherein said carbon dioxide indicating means includes:

chemical substance means for changing color when exposed to breath containing carbon dioxide; and internal chamber means in communication with said passageway means of the housing for receiving a predetermined amount of said chemical substance means so that said chemical substance means changes color at a rate which enables the level of carbon dioxide in the patient's breath to be determinable by measuring the length of the period over which said chemical substance means changes color, the level of carbon dioxide in the patient's breath thereby providing an indication of the patient's circulatory status.

6. An apparatus as claimed in claim 5 wherein said means for indicating the presence of carbon dioxide includes breath transmitting filter means for retaining said chemical substance means in said internal chamber means.

7. An apparatus as claimed in claim 6 wherein said filter means includes a cooper screen having mesh ranging between #40 and #80.

8. An apparatus as claimed in claim 5 wherein the length of the period over which the predetermined amount of said chemical substance means in said chamber means changes color is inversely proportional to the level of carbon dioxide in the patient's breath.

9. An apparatus as claimed in claim 8 wherein the length of the period is at least thirty seconds when said chemical substance means in said chamber means is exposed to breath containing about 1% carbon dioxide.

10. An apparatus as claimed in claim 8 wherein the length of the period is about four minutes when said chemical substance means in said chamber means is exposed to breath containing about 1% carbon dioxide.

11. An apparatus as claimed in claim 10 wherein said internal chamber means is cylindrically shaped and filled with said chemical substance means so as to provide a column of said chemical substance means that changes color along the column when exposed to breath of the patient containing carbon dioxide, said indicating means further including scale means calibrated with time indicating marks located on said internal chamber means along said column for indicating whether the patient's breath contains at least 1% carbon dioxide, the 1% level of carbon dioxide being indicated if that portion of the column indicated by said time indicating mark changes color in a period of time that is equal to or less than the time indicated for said time indicating mark.

12. An apparatus as claimed in claim 5 further comprising:

removable sealing means for sealing said internal chamber means to prevent said chemical substance means from being exposed to carbon dioxide until said removable sealing means is removed from said apparatus.

13. An apparatus as claimed in claim 12 wherein said internal chamber means has a sealable end in communication with said passageway means and wherein said removable sealing means includes a sealing pull tab which is sized and configured and provided with a suitable adhesive on one side thereof to sealingly cover said sealable end of said internal chamber means, said sealing tab also being provided with a tab end extending out of said apparatus to enable said tab end to be grasped and thereby removed when it is desired to use said apparatus.

14. An apparatus for monitoring patient's circulatory status during cardiopulmonary resuscitation comprising:

a housing defining passageway means for passing the patient's breath; and carbon dioxide indicating means in communication with said passageway means for indicating the presence of carbon dioxide in the patient's breath over a temporary period wherein the length of the temporary period of indicating is a known function of the level of carbon dioxide in the patient's breath so that the carbon dioxide level is determinable by measuring the length of the temporary period, said indicating means including chemical substance means for changing color when exposed to carbon dioxide, said indicating means also including internal chamber means in communication with said passageway means for receiving a predetermined amount of said chemical substance means so that all of said chemical substance means changes color at a predetermined rate which is proportional to the level of carbon dioxide in the patient's breath so that the level of carbon dioxide in the patient's breath is determinable by measuring the length of the period over which said chemical substance means changes color, the level of carbon dioxide in the patient's breath thereby providing an indication of the patient's circulatory status.

15. An apparatus as claimed in claim 14 wherein said chemical substance means includes an acid-base indicator and an amine.

16. An apparatus as claimed in claim 14 wherein said chemical substance means includes thymol blue and ethanol amine.

17. An apparatus as claimed in claim 14 wherein the length of the period over which the predetermined amount of chemical substance means in said chamber means changes color is about four minutes when said chemical substance means is exposed to breath of the patient containing about 1% carbon dioxide.

18. A method for monitoring a patient's circulatory status during cardiopulmonary resuscitation, said method comprising the steps of:
   providing resuscitation means for resuscitating the patient, the resuscitation means having breath passing means for passing the patient's breath;
   resuscitating the patient with the resuscitation means;
   providing an apparatus for attachment to the breath passing means of the resuscitation means, the apparatus including:
      a housing defining passageway means for passing the patient's breath which is in communication with the breath passing means of the resuscitation means when the apparatus is attached to the resuscitation means; and
      carbon dioxide indicating means in communication with the passageway means for indicating the presence of carbon dioxide in the patient's breath over a temporary period wherein the length of the temporary period is a known function of the level of carbon dioxide in the patient's breath;
   attaching the apparatus to the resuscitation means so that the patient'breath passes into the passageway means of the apparatus and contacts the carbon dioxide indicating means, such contact beginning the temporary period over which the indicating means indicates the presence of carbon dioxide; and
   measuring the length of the temporary period to determine the level of carbon dioxide in the patient's breath, the level of carbon dioxide thereby providing an indication of the patient's circulatory status.

* * * * *